US012431233B2

(12) United States Patent
Jameson et al.

(10) Patent No.: US 12,431,233 B2
(45) Date of Patent: Sep. 30, 2025

(54) TECHNIQUES FOR ACTIVITY GOAL PERSONALIZATION

(71) Applicant: Oura Health Oy, Oulu (FI)

(72) Inventors: Maris Alexandra Jameson, Encinitas, CA (US); Colleen Diane Simms, Scottsdale, AZ (US); Andy Campbell Roth, Long Beach, CA (US); Jake Harris Sherman, Portland, OR (US)

(73) Assignee: Oura Health Oy, Oulu (FI)

( * ) Notice: Subject to any disclaimer, the term of this patent is extended or adjusted under 35 U.S.C. 154(b) by 107 days.

(21) Appl. No.: 18/457,698

(22) Filed: Aug. 29, 2023

(65) Prior Publication Data

US 2024/0071597 A1 Feb. 29, 2024

Related U.S. Application Data

(60) Provisional application No. 63/402,364, filed on Aug. 30, 2022.

(51) Int. Cl.
*G16H 20/30* (2018.01)
*A61B 5/00* (2006.01)
*A61B 5/0205* (2006.01)
*A61B 5/11* (2006.01)

(52) U.S. Cl.
CPC ......... *G16H 20/30* (2018.01); *A61B 5/02055* (2013.01); *A61B 5/1118* (2013.01); *A61B 5/4815* (2013.01); *A61B 5/6826* (2013.01); *A61B 5/742* (2013.01)

(58) Field of Classification Search
CPC ........ G16H 20/30; G16H 15/00; G16H 40/67; G16H 50/70; G16H 40/63; G16H 50/30; A61B 5/02055; A61B 5/1118; A61B 5/4815; A61B 5/6826; A61B 5/742; A61B 5/02438; A61B 5/4866; A61B 5/74
See application file for complete search history.

(56) References Cited

U.S. PATENT DOCUMENTS

| | | | | |
|---|---|---|---|---|
| 2013/0110264 A1* | 5/2013 | Weast | ................... | H04B 1/385 |
| | | | | 700/91 |
| 2014/0244009 A1* | 8/2014 | Mestas | .................. | G16H 40/63 |
| | | | | 700/91 |
| 2014/0266731 A1* | 9/2014 | Malhotra | ................ | G06F 1/163 |
| | | | | 340/573.1 |
| 2021/0401378 A1* | 12/2021 | Pho | ....................... | A61B 5/0008 |
| 2022/0110547 A1* | 4/2022 | Kinnunen | .......... | A61B 5/02416 |

* cited by examiner

*Primary Examiner* — Chinyere Mpamugo
(74) *Attorney, Agent, or Firm* — Holland & Hart LLP

(57) ABSTRACT

Methods, systems, and devices for activity goal personalization are described. A user device may receive physiological data associated with a user from a wearable device. The user device may compute a recovery metric for the user based at least in part on the received physiological data. The user device may receive an input adjusting a baseline activity level for the user within an application running on the user device and associated with the wearable device. The user device may compute a target activity level for the user based at least in part on the adjusted baseline activity level and the computed recovery metric for the user, and cause a graphical user interface (GUI) of the user device running the application to display the computed target activity level for the user.

20 Claims, 8 Drawing Sheets

TECHNIQUES FOR ACTIVITY GOAL PERSONALIZATION

CROSS REFERENCE

The present Application for Patent claims the benefit of U.S. Provisional Patent Application No. 63/402,364 by Jameson et al., entitled "TECHNIQUES FOR ACTIVITY GOAL PERSONALIZATION," filed Aug. 30, 2022, which is assigned to the assignee hereof and expressly incorporated by reference herein.

FIELD OF TECHNOLOGY

The following relates to wearable devices and data processing, including techniques for activity goal personalization.

BACKGROUND

Some devices may be configured to collect personal data from users. For example, a device may include one or more sensors that collect physiological data (also referred to as biometric data) from a user. Some devices may be able to perform various actions, such as providing certain goals to the user based at least in part on the collected physiological data. In the example of health and wellness, these devices may provide health and wellness goals using the collected physiological data. However, improved techniques for providing health and wellness goals to a user may be desired.

DETAILED DESCRIPTION

Figure 1:
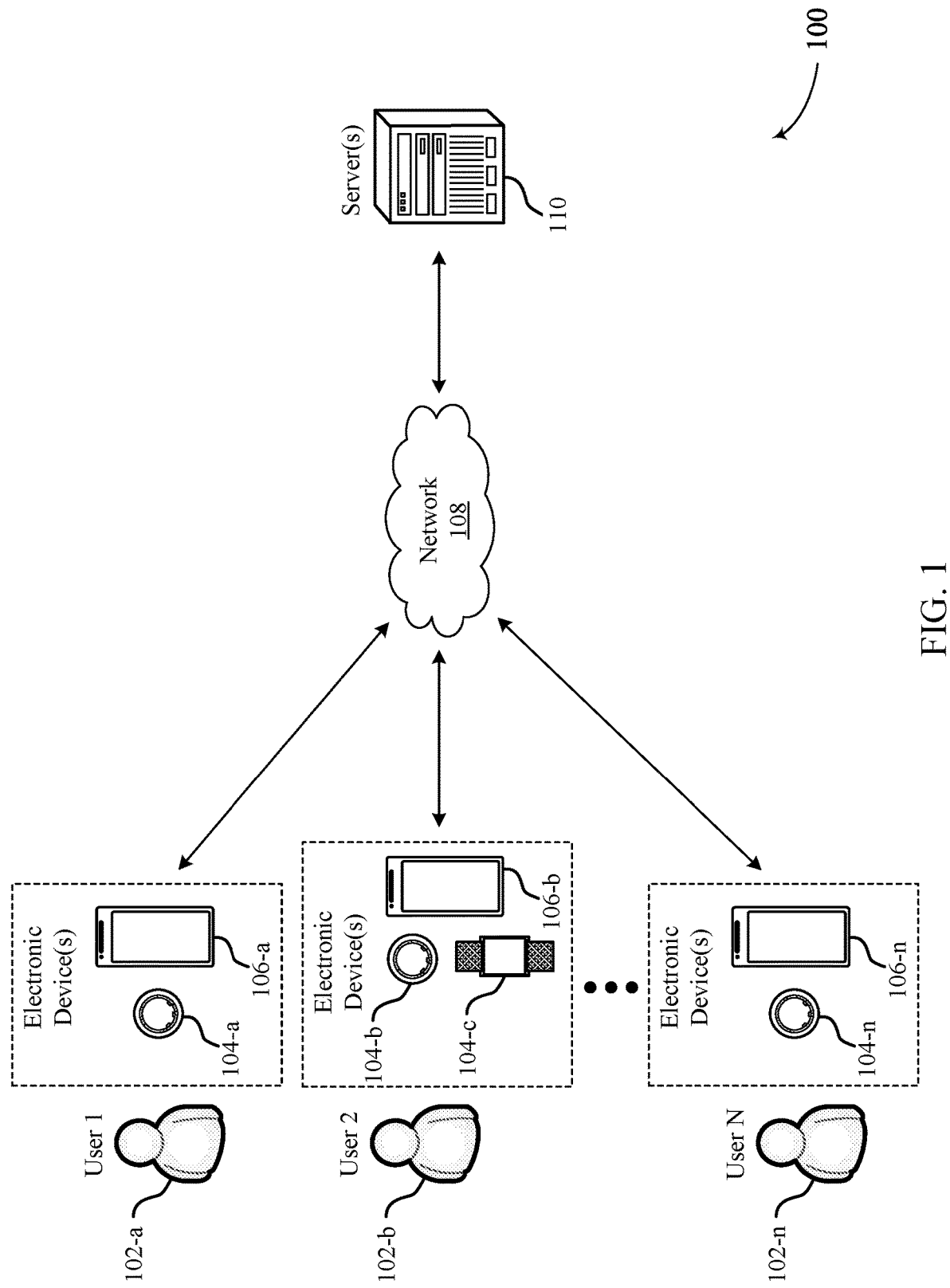
FIG. 1 illustrates an example of a system that supports techniques for activity goal personalization in accordance with aspects of the present disclosure.

Various applications may collect physiological data associated with a user to provide an activity goal (also referred to as an activity level) relevant to the user. In some cases, an application associated with health and wellness may collect and track physiological data, and the like. For example, a health and wellness application may include information associated with a user's physiological history, and the like. In some other cases, a health and wellness application may be configured to provide an activity goal to a user based on the user's physiological history. For example, a health and wellness application may provide an active calorie burn goal, or the like to improve the health and wellness of the user. Some applications for providing activity goals to a user may fail to provide the most effective activity goals, based on changes in the user's lifestyle, and in improving the health and wellness of the user. As such, improvements to these health and wellness applications for providing activity goals that are intended to have a health and wellness impact on a user are needed.

A system including a user device and a wearable device may collect physiological data and, based on the collected physiological data, may compute a target activity goal for the user. The wearable device (e.g., a wearable ring) may collect physiological data associated with the user using one or more sensors of the wearable device. The physiological data may include heart rate data associated with the user, heart rate variability data associated with the user, temperature data associated with the user, respiratory rate data associated with the user, blood oxygen data associated with the user, sleep data associated with the user, activity data associated with the user, or any combination thereof.

In some implementations, collected or received physiological data associated with the user may be used, for example, by the user device to compute a Readiness Score (e.g., a recovery metric) for the user and, based on the collected or received physiological data associated with the user and the computed Readiness Score for the user, the user device may compute a target activity goal for the user. For example, the collected or received physiological data associated with the user and the computed Readiness Score for the user may be used by the user device to compute an active calorie burn goal (e.g., a daily calorie burn target) for the user. Alternatively, or additionally, the collected or received physiological data associated with the user and the computed Readiness Score for the user may be used by the user device to compute an active step count goal (e.g., a daily step target) for the user.

To provide improvements to activity goals that are intended to have a health and wellness impact on a user, the user may adjust a baseline activity goal (also referred to as a baseline activity level) for the user that better aligns with the user's changing lifestyle. Put another way, the user may increase or decrease the baseline activity goal based on changes in the user's lifestyle (e.g., routine). For example, the user device may receive an input (e.g., from the user) adjusting a baseline activity goal for the user within an application (e.g., a health and wellness application) running on the user device and associated with the wearable device of the user. By enabling the user device to provide adjustments to baseline activity goals, the user device may compute a target activity goal for the user that better aligns with the user's changing lifestyle.

In some implementations, the user may also select or change an activity goal type within the application (e.g., a health and wellness application) running on the user device and associated with the wearable device of the user. For example, the user may select the activity goal type to be an active calorie burn goal or an active step count goal and, based on the selected activity goal type, the user device may compute a target activity goal for the user that better aligns with the user's lifestyle and activity goal type. In some other implementations, the user may select multiple activity goal types within the application (e.g., a health and wellness application) running on the user device and associated with the wearable device of the user. For example, the user may select both an active calorie burn goal and an active step count goal and, based on the selected activity goal types, the user device may compute target activity goals for the user that better align with the user's lifestyle and activity goal types. Other examples of activity goal types may include, but is not limited to, a heart rate goal (e.g., a target heart rate for the user to meet, such as equal to or greater than a threshold), an activity goal including a duration goal for engaging in the activity goal (e.g., minutes or hours of a certain activity the user is to engage in, such as cycling, swimming, or the like), among other examples. By enabling the user device to provide different activity goal types, the user device may compute a target activity goal for the user that better aligns with the user's interest (e.g., tracking an active calorie burn goal, tracking active step count goal, or the like).

For example, the user device may compute a target activity goal for the user based at least in part on the adjusted baseline activity goal, the selected activity goal type, and the computed Readiness Score for the user. Put another way, based on changes in the user's Readiness Score and the user's lifestyle, the user device may be enabled to compute and provide a target activity goal that is more appropriate for the user. The Readiness Score, in some implementations, may be computed based on information specific to the user, such as gender, height, weight, age, body type, and the like.

In some implementations, the user device may determine insights and content for recommending to the user based at least in part on the physiological data, the computed Readiness Score, or the computed target activity goal, or any combination thereof. Based on the determination, the user device may determine (e.g., select) insights and content that may provide guidance to the user on regulating (e.g., increasing, decreasing, managing, or any combination thereof) a physiological state of the user, providing guidance to the user on improving the user's Readiness Score, or providing guidance on meeting the user's target activity goal, or any combination thereof.

As a result, the system facilitates improvements to the user's health and wellness by providing personalized activity goals, as well as health and wellness insights. While much of the present disclosure is described in the context of activity goals, this is not to be regarded as a limitation of the present disclosure. In particular, techniques described herein may enable health and wellness insights for a user that may help the user achieve target activity goals for the user. Moreover, physiological data associated with a user may be used to update any score, measure, metric, or other abstraction associated with a user's health or activity.

Aspects of the disclosure are initially described in the context of systems supporting physiological data collection from users via wearable devices. Additional aspects of the disclosure are described in the context of example GUIs. Aspects of the disclosure are further illustrated by and described with reference to apparatus diagrams, system diagrams, and flowcharts that relate to techniques for activity goal personalization.

FIG. 1 illustrates an example of a system 100 that supports techniques for activity goal personalization in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some that may measure physiological parameters and some that may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time that the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for activity goal personalization. In particular, the system 100 illustrated in FIG. 1 may support techniques for providing activity goals and insights to a user 102 by causing a user device 106 corresponding to the user 102 to display target activity goals to the user 102. For example, as shown in FIG. 1, a User 1 (e.g., a user 102-*a*) may be associated with a wearable device 104-*a* (e.g., a ring 104-*a*) and a user device 106-*a*. The wearable device 104-*a* (e.g., a ring 104-*a*) may receive physiological data associated with the User 1 (e.g., the user 102-*a*). The physiological data may include heart rate data associated with the User 1 (e.g., the user 102-*a*), heart rate variability data associated with the User 1 (e.g., the user 102-*a*), temperature data associated with the User 1 (e.g., the user 102-*a*), respiratory rate data associated with the User 1 (e.g., the user 102-*a*), blood oxygen data associated with the User 1 (e.g., the user 102-*a*), sleep data associated with the User 1 (e.g., the user 102-*a*), activity data associated with the User 1 (e.g., the user 102-*a*), or any combination thereof.

In some implementations, collected or received physiological data associated with the User 1 (e.g., the user 102-*a*) may be used, for example, by the user device 106 (e.g., the user device 106-*a*) associated with the User 1 (e.g., the user 102-*a*) to compute a recovery metric (e.g., Readiness Score) for the User 1 (e.g., the user 102-*a*). In some other implementations, any of the components of the system 100, including the wearable device 104-*a* (e.g., a ring 104-*a*), the user device 106-*a* associated with User 1 (e.g., a user 102-*a*), the one or more servers 110, or any combination thereof, may compute a recovery metric (e.g., Readiness Score) for the User 1 (e.g., the user 102-*a*), for example, based on collected or received physiological data associated with the User 1 (e.g., the user 102-*a*).

In some implementations, collected or received physiological data associated with the User 1 (e.g., the user 102-*a*) may be used, for example, by the user device 106 (e.g., the user device 106-*a*) associated with the User 1 (e.g., the user 102-*a*) to compute a Sleep Score for the User 1 (e.g., the user 102-*a*). In some other implementations, any of the components of the system 100, including the wearable device 104-*a* (e.g., a ring 104-*a*), the user device 106-*a* associated with User 1 (e.g., a user 102-*a*), the one or more servers 110, or any combination thereof, may compute a Sleep Score for the User 1 (e.g., the user 102-*a*), for example, based on collected or received physiological data associated with the User 1 (e.g., the user 102-*a*)

In the system 100, the user device 106-*a* may receive an input adjusting a baseline activity goal (also referred to a baseline activity level) for the User 1 (e.g., the user 102-*a*) within an application running on the user device 106-*a* and associated with the wearable device 104-*a* (e.g., the ring 104-*a*). An application running fully or partially (e.g., in the case of a cloud application) on the user device 106-*a* may be a lifestyle application (e.g., fitness, food, a journal, travel, or the like), or the like. In some implementations, any of the components of the system 100, including the wearable device 104-*a* (e.g., a ring 104-*a*), the user device 106-*a* associated with User 1 (e.g., a user 102-*a*), the one or more servers 110, or any combination thereof, may receive an input to adjust a baseline activity goal for the User 1 (e.g., the user 102-*a*) within an application running on the user device 106-*a* and associated with the wearable device 104-*a* (e.g., the ring 104-*a*).

In some implementations, adjusting a baseline activity goal for the User 1 (e.g., the user 102-*a*) within an application running on the user device 106-*a* and associated with the wearable device 104-*a* (e.g., the ring 104-*a*) may include increasing the baseline activity goal for the User 1 (e.g., the user 102-*a*) from a default baseline activity goal for the User 1 (e.g., the user 102-*a*). In some other implementations, adjusting a baseline activity goal for the User 1 (e.g., the user 102-*a*) within an application running on the user device 106-*a* and associated with the wearable device 104-*a* (e.g., the ring 104-*a*) may include decreasing the baseline activity goal for the User 1 (e.g., the user 102-*a*) from a default baseline activity goal for the User 1 (e.g., the user 102-*a*). The default baseline activity goal for the User 1 (e.g., the user 102-*a*) may be a recommended activity goal that may be computed, based at least in part on the computed recovery metric (e.g., Readiness Score) for the User 1 (e.g., the user 102-*a*), by any of the components of the system 100, including the wearable device 104-*a* (e.g., a ring 104-*a*), the user device 106-*a* associated with User 1 (e.g., a user 102-*a*), the one or more servers 110, or any combination thereof.

In the system 100, the user device 106-*a* may compute a target activity goal (also referred to as a target activity level) for the User 1 (e.g., the user 102-*a*) based at least in part on the adjusted baseline activity goal and the computed recovery metric for the User 1 (e.g., the user 102-*a*). The user device 106-*a* may cause a GUI of the user device 106-*a* running the application to display the computed target activity goal for the User 1 (e.g., the user 102-*a*). In some implementations, any of the components of the system 100, including the wearable device 104-*a* (e.g., a ring 104-*a*), the user device 106-*a* associated with User 1 (e.g., a user 102-*a*), the one or more servers 110, or any combination thereof, may compute a target activity goal (also referred to as a target activity level) for the User 1 (e.g., the user 102-*a*) based at least in part on the adjusted baseline activity goal and the computed recovery metric for the User 1 (e.g., the user 102-*a*).

Additionally, in some implementations, the user device 106-*a* may compute a Sleep Score for the user based at least in part on the received physiological data, and compute a target activity goal for the User 1 (e.g., the user 102-*a*) based at least in part on the Sleep Score. In some implementations, any of the components of the system 100, including the wearable device 104-*a* (e.g., a ring 104-*a*), the user device 106-*a* associated with User 1 (e.g., a user 102-*a*), the one or more servers 110, or any combination thereof, may compute a target activity goal for the User 1 (e.g., the user 102-*a*) based at least in part on the Sleep Score.

In the system 100, the user device 106-*a* may cause a GUI of the user device 106-*a* to display a set of activity goals. The set of activity goals may include one or more activity goals that are different than the baseline activity goal for the User 1 (e.g., the user 102-*a*). For example, each activity goal of the set of activity goals may be based at least in part on a factor (e.g., a multiple) of the baseline activity goal for the User 1 (e.g., the user 102-*a*). The user device 106-*a* may adjust the baseline activity goal for the User 1 (e.g., the user 102-*a*) based at least in part on a selected at least one activity goal from the set of activity goals. In some implementations, the selected at least one activity goal from the set of activity goals may be based at least in part on receiving, via the GUI of the user device 106-*a*, a selection of at least one activity goal by the User 1 (e.g., the user 102-*a*). For example, the user device 106-*a* may display, via the GUI of the user device 106-*a*, a selectable graphical element and the User 1 (e.g., the user 102-*a*) may select the at least one activity goal from the set of activity goals based at least in part on the selectable graphical element. In some implementations, the selectable graphical element may be a slider control configured to slide along a slider track of the GUI of the user device 106-*a*. The user device 106-*a* may detect the input adjusting the baseline activity level based on the slider track of the GUI of the user device 106-*a*. Each activity goal of the set of activity goals may, for example, correspond to a respective node on the slider track of the GUI of the user device 106-*a*.

Additionally, or alternatively, the user device 106-*a* may cause a GUI of the user device 106-*a* running the application to display a set of activity goal types for the User 1 (e.g., the user 102-*a*). The set of activity goal types may include, for example, a calorie count for the User 1 (e.g., the user 102-*a*) or a step count for the User 1 (e.g., the user 102-*a*). As such, the user device 106-*a* may provide options to the User 1 (e.g., the user 102-*a*) for selecting a type of activity goal for tracking a health and wellness of the User 1 (e.g., the user 102-*a*). For example, the User 1 (e.g., the user 102-*a*) may select a calorie count goal (e.g., an active calorie burn goal). The user device 106-*a* may then compute a calorie count goal for the User 1 (e.g., the user 102-*a*) based at least in part on the received physiological data from the wearable device 104-*a* (e.g., the ring 104-*a*), the computed recovery metric for the User 1 (e.g., the user 102-*a*), the computed Sleep Score for the User 1 (e.g., the user 102-*a*), the adjusted baseline activity goal for the User 1 (e.g., the user 102-*a*), or any combination thereof. Alternatively, the User 1 (e.g., the user 102-*a*) may select a step count goal and the user device 106-*a* may then compute a step count goal for the User 1 (e.g., the user 102-*a*) based at least in part on the received physiological data from the wearable device 104-*a* (e.g., the ring 104-*a*), the computed recovery metric for the User 1 (e.g., the user 102-*a*), the computed Sleep Score for the User 1 (e.g., the user 102-*a*), the adjusted baseline activity goal for the User 1 (e.g., the user 102-*a*), or any combination thereof.

In some implementations, the user device 106-*a* may toggle displaying information associated with an activity goal within the application running on the user device 106-*a*. For example, the user device 106-*a* may toggle displaying a calorie count (e.g., an active calorie burn) for the User 1 (e.g., the user 102-*a*) within the application running on the user device 106-*a* and associated with the wearable device 104-*a* (e.g., the ring 104-*a*). In some implementations, the user device 106-*a* may enable the application to display the computed calorie count goal for the User 1 (e.g., the user 102-*a*) within the application running on the user device 106-*a* and associated with the wearable device 104-*a* (e.g., the ring 104-*a*) based at least in part on a setting (e.g., an ON/OFF setting in the application running on the user device 106-*a*) for displaying the calorie count for the User 1 (e.g., the user 102-*a*). The user device 106-*a* may then cause a GUI of the user device 106-*a* running the application to display the computed target activity goal for the User 1 (e.g., the user 102-*a*) and the computed calorie count for the User 1 (e.g., the user 102-*a*) based at least in part on the enabling.

In some other implementations, the user device 106-*a* may disable the application from displaying the computed calorie count goal for the User 1 (e.g., the user 102-*a*) within the application running on the user device 106-*a* and associated with the wearable device 104-*a* (e.g., the ring 104-*a*) based at least in part on a setting for displaying the calorie count goal for the User 1 (e.g., the user 102-*a*). Put another way, the user device 106-*a* may cause a GUI of the user device 106-*a* running the application to display the computed target activity goal for the User 1 (e.g., the user 102-*a*) irrespective of the computed calorie count for the User 1 (e.g., the user 102-*a*) based at least in part on the disabling. As such, the user device 106-*a* may refrain from displaying the computed calorie count for the User 1 (e.g., the user 102-*a*) within the application running on the user device 106-*a* and associated with the wearable device 104-*a* (e.g., the ring 104-*a*).

Accordingly, in the system 100, any of the components of the system 100, including the wearable device 104-*a* (e.g., a ring 104-*a*), the user device 106-*a* associated with User 1 (e.g., a user 102-*a*), the one or more servers 110, or any combination thereof, may provide activity goals for a user that better align with the user's lifestyle and preferences. Additionally, in the system 100, any of the components of the system 100, including the wearable device 104-*a* (e.g., a ring 104-*a*), the user device 106-*a* associated with User 1 (e.g., a user 102-*a*), the one or more servers 110, or any combination thereof, may provide insights for improving or managing the health and wellness of the user 102.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
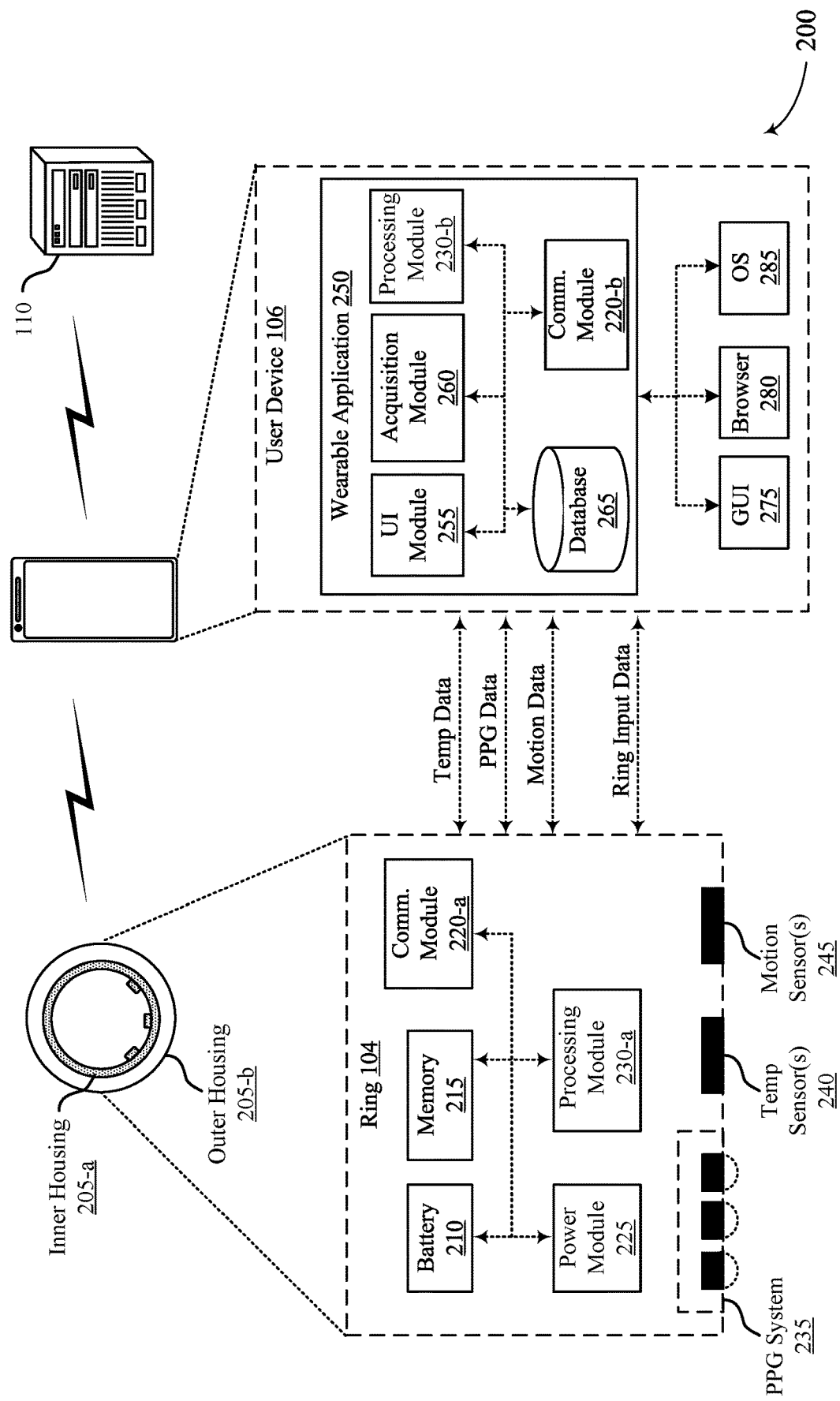
FIG. 2 illustrates an example of a system that supports techniques for activity goal personalization in accordance with aspects of the present disclosure.

FIG. 2 illustrates an example of a system 200 that supports techniques for activity goal personalization in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, as such the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate may be stored in memory 215 and may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall recovery metric (e.g., Readiness Score) may be calculated based on a set of contributors, including: sleep, sleep balance, heart rate, HRV balance, recovery index, temperature, activity, activity balance, or any combination thereof. The recovery metric may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for activity goal personalization. In particular, the system 200 illustrated in FIG. 2 may support techniques for providing activity goals and insights to a user by causing a user device 106 corresponding to the user to display, via the GUI 275, activity goals and insights for the user. The ring 104 may receive physiological data of a respective user associated with the ring 104. The physiological data may include heart rate data, respiratory rate data, sleep data, activity data, or any combination thereof. In some implementations, collected or received physiological data of a respective user associated with the ring 104 may be used, for example, by the user device 106 associated with the user to compute a recovery metric (e.g., Readiness Score). In some other implementations, collected or received physiological data of a respective user associated with the ring 104 may be used, for example, by the user device 106 associated with the user to also compute a Sleep Score.

Additionally, or alternatively, in the system 200, the user device 106 may receive an input adjusting a baseline activity goal (also referred to a baseline activity level) associated with the respective user. In some implementations, adjusting (e.g., based on the processing module 230-*b*) a baseline activity goal for the respective user within an application running on the user device 106 and associated with the ring 104 may include increasing (e.g., based on the processing module 230-*b*) the baseline activity goal for the respective user from a default baseline activity goal. In some other implementations, adjusting (e.g., based on the processing module 230-*b*) a baseline activity goal for the respective user within an application running on the user device 106 and associated with the ring 104 may include decreasing (e.g., based on the processing module 230-*b*) the baseline activity goal for the respective user from a default baseline activity goal.

In the system 200, the user device 106 (e.g., based on processing module 230-*b*) may compute a target activity goal (also referred to as a target activity level) for the respective user based at least in part on the adjusted baseline activity goal and the computed recovery metric for the respective user. Additionally, the user device 106 (e.g., based on the processing module 230-*b*) may compute a target activity goal for the respective user based at least in part on the adjusted baseline activity goal and the computed Sleep Score for the respective user. The user device 106 may cause the GUI 275 of the user device 106 running the application to display the computed target activity goal for the respective user. Accordingly, in the system 200, any of the components of the system 200, including the ring 104 or the user device 106, or any combination thereof, may provide personalized activity goals and insights for improving or managing the health and wellness for a respective user.

Figure 3:
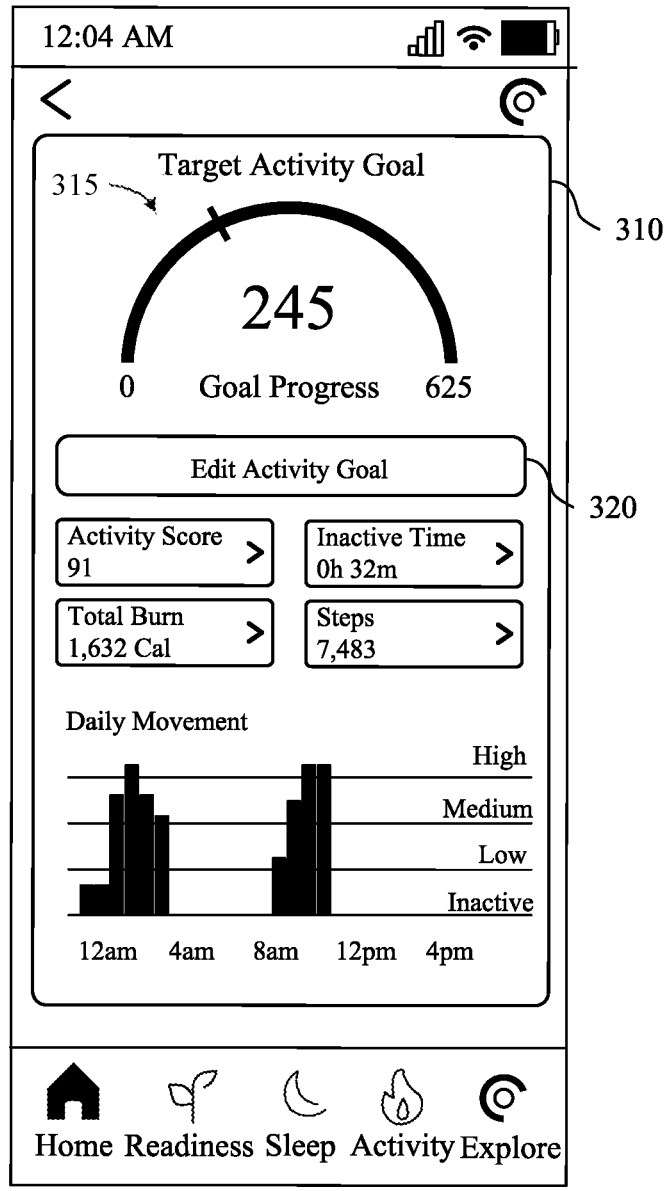
FIG. 3 illustrates an example of a graphical user interface (GUI) that supports techniques for activity goal personalization in accordance with aspects of the present disclosure.

FIG. 3 illustrates an example of a GUI 300 that supports techniques for activity goal personalization in accordance with aspects of the present disclosure. The GUI 300 may implement, or be implemented by, aspects of the system 100 or the system 200, or any combination thereof. In some examples, the GUI 300 may be an example of a GUI of a user device that may be examples of GUIs and user devices as described with reference to FIGS. 1 and 2. For example, the GUI 300 may be an example of a GUI 275 of a user device 106 as described with reference to FIG. 2. In the example of FIG. 3, the GUI 300 may include an application interface 305 that may be displayed to a user 102 via the GUI 300.

The application interface 305 may include a set of graphical elements that an application running on a user device 106 provides so that a user 102 may provide input to, and receive output from, the application via the application interface 305. In some examples, one or more operations associated with the GUI 300 may be performed based on a manipulation of the one or more graphical elements associated with the GUI 300. Examples of graphical elements associated with the GUI 300 may include, but are not limited to, buttons, sliders, droplists, tabs, text boxes, and the like. The application interface 305 may also include a set of graphical elements enabling the user 102 to switch between different features of the application interface 305. For example, the set of graphical elements may allow the user 102 to switch between one or more of a "Home" feature, a "Readiness" feature, a "Sleep" feature, an "Activity" feature, or an "Explore" feature, within the application running on the user device 106.

In the example of FIG. 3, physiological data collected from a wearable device 104 associated with the user 102 may be used by the user device 106 to compute a Readiness Score for the user 102. The computed Readiness Score for the user 102 may be used to compute a target activity goal for the user 102. In some other implementations, physiological data collected from the wearable device 104 associated with the user 102 may be used by the user device 106 to compute a Sleep Score for the user 102. Additionally, or alternatively, the computed Sleep Score for the user 102 may be used to compute the target activity goal for the user 102. The target activity goal may be displayed to the user via the GUI 300, as shown in the application interface 305. For example, the application interface 305 may include a graphical element 310 that may display a Target Activity Goal 315.

In some implementations, a target activity goal may be dynamic for the user 102. For example, the user device 106 may change a target activity goal for the user 102 based at least in part on a Readiness Score for the user 102. In some implementations, the user device 106 may increase the target activity goal from a baseline activity goal based at least in part on the computed Readiness Score for the user 102 satisfying a threshold. For example, if the computed Readiness Score for the user 102 is greater than or equal to a threshold (e.g., Readiness Score ≥69%), the user device 106 may increase the target activity goal based at least in part on the computed Readiness Score. In some implementations, the target activity goal may be increased by a factor proportional to the computed Readiness Score. In some other implementations, the user device 106 may decrease the target activity goal from a baseline activity goal based at least in part on the computed Readiness Score for the user 102 satisfying a threshold. For example, if the computed Readiness Score for the user 102 is less than or equal to a threshold (e.g., Readiness Score ≤85%), the user device 106 may decrease the target activity goal based at least in part on the computed Readiness Score. In some implementations, the target activity goal may be decreased by a factor proportional to the computed Readiness Score. In other implementations, the user device 106 may refrain from adjusting the target activity goal for the user 102 from a baseline activity goal for the user 102 based at least in part on the computed Readiness Score being within a threshold range (e.g., 70%≤Readiness Score≤84%).

In the example of FIG. 3, the Target Activity Goal 315 may be for the user 102 to burn a target active calories (e.g., 625 active calories). In some implementations, the graphical element 310 may also display a "Goal Progress" associated with the Target Activity Goal 315. For example, the "Goal Progress" may display a status of the Target Activity Goal 315, such as showing that the user 102 has burned 245 calories out of the 625 calories for the computed Target Activity Goal 315 for the user 102. Additionally, in the example of FIG. 3, the graphical element 310 may display other information, such as an "Activity Score" associated with the user 102, an "Inactive Time" associated with the user 102, a "Total Burn" associated with the user 102, "Steps" associated with the user 102, or "Daily Movements" associated with the user 102, or any combination thereof.

In some cases, the user 102 may want to align a target activity goal with the user's 102 lifestyle. In some cases, the user 102 may be wanting for more control over a target activity goal and guidance on how to set the right type of target activity goal. As described herein, the Target Activity Goal 315 may be computed based at least in part on an adjusted baseline activity goal and the computed Readiness Score for the user 102 and/or the computed Sleep Score for the user 102. For example, the user 102 may adjust a baseline activity goal via the GUI 300 by selecting (e.g., clicking, touching, etc.) the graphical element 320—"Edit Activity Goal"—displayed via the GUI 300. By selecting the graphical element 320—"Edit Activity Goal"—the user 102 may adjust a baseline activity goal and other information as further described with reference to FIG. 4.

Figure 4:
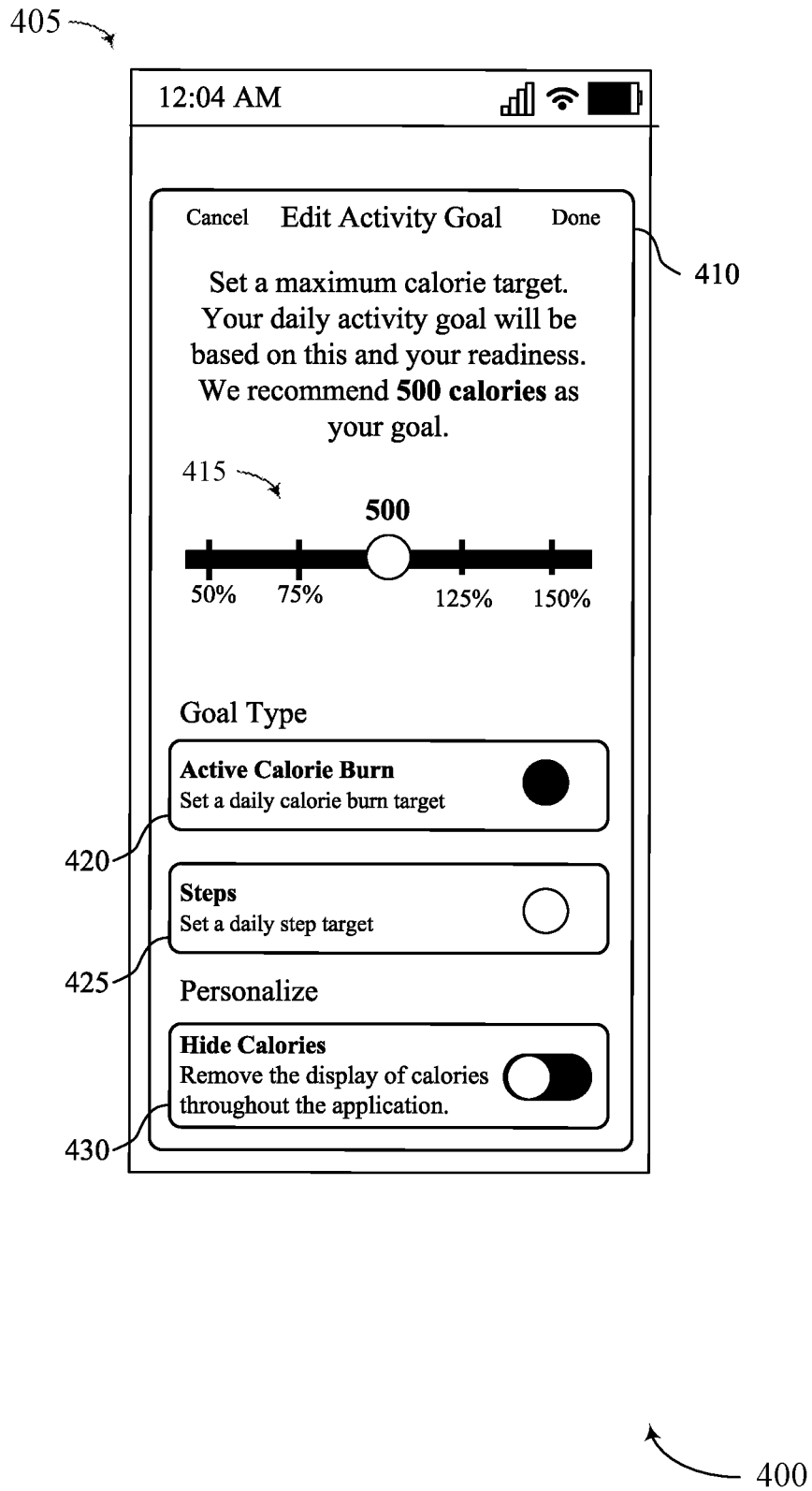
FIG. 4 illustrates an example of a GUI that supports techniques for activity goal personalization in accordance with aspects of the present disclosure.

FIG. 4 illustrates an example of a GUI 400 that supports techniques for activity goal personalization in accordance with aspects of the present disclosure. The GUI 400 may implement, or be implemented by, aspects of the system 100 or the system 200, or any combination thereof. In some examples, the GUI 400 may be an example of a GUI of a user device that may be examples of GUIs and user devices as described with reference to FIGS. 1 and 2. For example, the GUI 400 may be an example of a GUI 275 of a user device 106 as described with reference to FIG. 2. In the example of FIG. 4, the GUI 400 may include an application interface 405 that may be displayed to a user 102 via the GUI 400.

The application interface 405 may be associated with an application running on the user device 106. In some examples, the application interface 405 may include a set of graphical elements that an application running on the user device 106 may provide (e.g., display) so that the user 102 may provide input to, and receive output from, the application via the application interface 405. In some examples, one or more operations associated with the GUI 400 may be performed based on a manipulation of the one or more graphical elements associated with the GUI 400. Examples of graphical elements associated with the GUI 400 may include, but are not limited to, buttons, sliders, droplists, tabs, text boxes, and the like.

The user device 106 may adjust a baseline activity goal and other information for the user 102 associated with a wearable device 104 and the user device 106 associated with the GUI 400. In the example of FIG. 4, the baseline activity goal for the user 102 may be computed to be 500 active calories, for example, based at least in part on received or collected physiological data associated with the user 102 and/or a computed Readiness Score for the user 102 and/or a computed Sleep Score for the user 102. Put another way, the user's 102 baseline activity goal may be to burn 500 active calories. In some cases, the user 102 may wish to adjust the user's 102 computed baseline activity goal.

The baseline activity goal may be adjusted, as shown in the application interface 405. For example, the application interface 405 may include a graphical element 410 that may display a slider control 415 configured to slide along a slider track of the GUI 400. The user 102 may select an adjusted baseline activity goal by manipulating the slider control 415 along the slider track of the GUI 400. In some implementations, the user 102 may increase or decrease the user's 102 baseline activity goal. Each activity level of the set of activity levels may be selectable at respective nodes along a minimum to maximum range of the GUI 400. In the example of FIG. 4, the user's 102 baseline activity goal may be adjusted to 50% of the user's 102 baseline activity goal, 75% of the user's 102 baseline activity goal, 125% of the user's 102 baseline activity goal, or 150% of the user's 102 baseline activity goal, or the like. As such, the adjusted baseline activity goal may be a multiple of the user's 102 recommended baseline activity goal.

Additionally, in the example of FIG. 4, the graphical element 410 may display other information, such as a "Goal Type" feature and a "Personalization" feature or any combination thereof. In some implementations, the user 102 may select a "Goal Type" by manipulating a graphical element 420 that may display an "Active Calorie Burn" 420 (e.g., a daily calorie burn target) as a "Goal Type." Alternatively, in some other implementations, the user 102 may select a "Goal Type" by manipulating a graphical element 425 that may display "Steps" 425 (e.g., a daily step target) as a "Goal Type." In some implementations, the baseline activity goal may be based at least in part on the selected "Goal Type." For example, if the user 102 selects the "Active Calorie Burn" 420 as the "Goal Type," the baseline activity goal may be in units of calories. Otherwise, if the user 102 selects the "Steps" 425 as the "Goal Type," the baseline activity goal may be in units of steps. In the example of FIG. 4, the user device 106 may hide calories from being displayed to the user 102, for example, based at least in part on the user 102 manipulating (e.g., toggling) the graphical element 430— "Hide Calories."

Therefore, the GUI 400 may be configured to support providing personalized activity goals. By providing personalized activity goals to the user 102, the user 102 may experience an improvement to the health and wellness of the user 102 (e.g., heart rate and the like).

Figure 5:
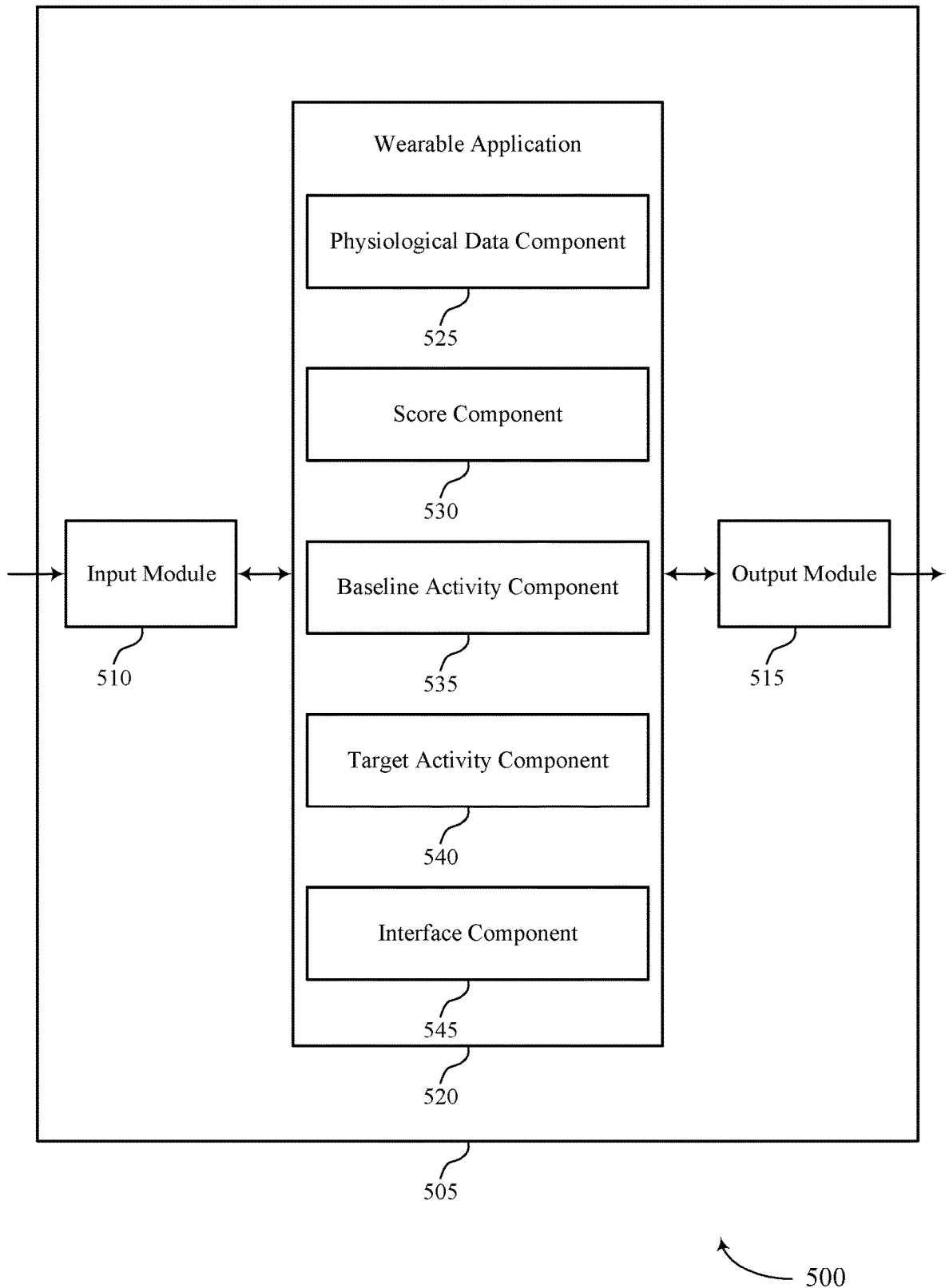
FIG. 5 shows a block diagram of an apparatus that supports techniques for activity goal personalization in accordance with aspects of the present disclosure.

FIG. 5 shows a block diagram 500 of a device 505 that supports techniques for activity goal personalization in accordance with aspects of the present disclosure. The device 505 may include an input module 510, an output module 515, and a wearable application 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable application 520 may include a physiological data component 525, a score component 530, a baseline activity component 535, a target activity component 540, an interface component 545, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The wearable application 520 may support activity goal personalization at a device in accordance with examples as disclosed herein. The physiological data component 525 may be configured as or otherwise support a means for receiving physiological data associated with a user from a wearable device. The score component 530 may be configured as or otherwise support a means for computing a recovery metric for the user based at least in part on the received physiological data. The baseline activity component 535 may be configured as or otherwise support a means for receiving an input adjusting a baseline activity level for the user within an application running on the device and associated with the wearable device. The target activity component 540 may be configured as or otherwise support a means for computing a target activity level for the user based at least in part on the adjusted baseline activity level and the computed recovery metric for the user. The interface component 545 may be configured as or otherwise support a means for causing a GUI of the device running the application to display the computed target activity level for the user.

Figure 6:
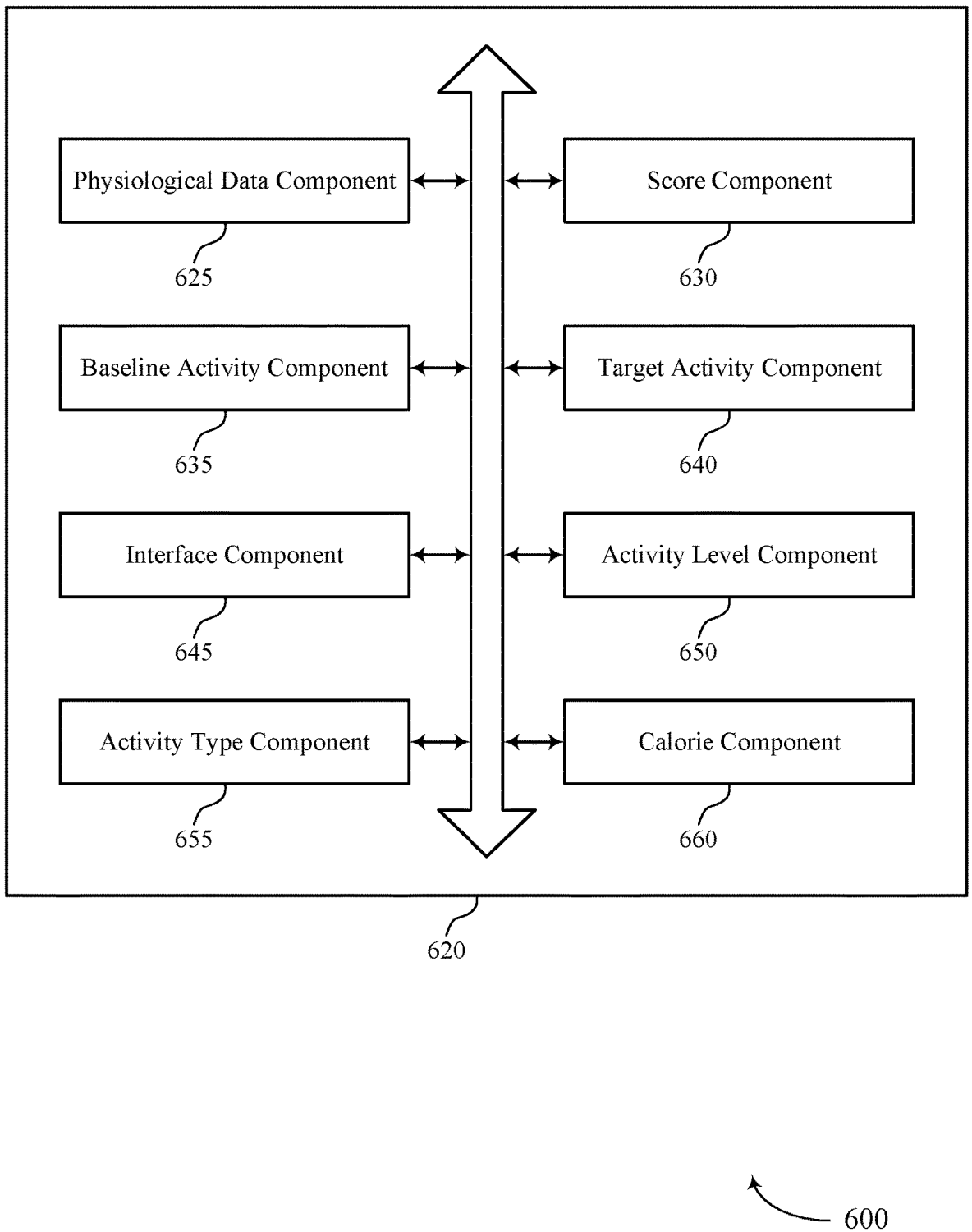
FIG. 6 shows a block diagram of a wearable application that supports techniques for activity goal personalization in accordance with aspects of the present disclosure.

FIG. 6 shows a block diagram 600 of a wearable application 620 that supports techniques for activity goal personalization in accordance with aspects of the present disclosure. The wearable application 620 may be an example of aspects of a wearable application or a wearable application 520, or both, as described herein. The wearable application 620, or various components thereof, may be an example of means for performing various aspects of techniques for activity goal personalization as described herein. For example, the wearable application 620 may include a physiological data component 625, a score component 630, a baseline activity component 635, a target activity component 640, an interface component 645, an activity level component 650, an activity type component 655, a calorie component 660, or any combination thereof. Each of these components may communicate, directly or indirectly, with one another (e.g., via one or more buses).

The wearable application 620 may support activity goal personalization at a device in accordance with examples as disclosed herein. The physiological data component 625 may be configured as or otherwise support a means for receiving physiological data associated with a user from a wearable device. The score component 630 may be configured as or otherwise support a means for computing a recovery metric for the user based at least in part on the received physiological data. The baseline activity component 635 may be configured as or otherwise support a means for receiving an input adjusting a baseline activity level for the user within an application running on the device and associated with the wearable device. The target activity component 640 may be configured as or otherwise support a means for computing a target activity level for the user based at least in part on the adjusted baseline activity level and the computed recovery metric for the user. The interface component 645 may be configured as or otherwise support a means for causing a GUI of the device running the application to display the computed target activity level for the user.

In some examples, the baseline activity component 635 may be configured as or otherwise support a means for receiving a second input to adjust the baseline activity level for the user within the application running on the device and associated with the wearable device. In some examples, the activity level component 650 may be configured as or otherwise support a means for causing the GUI to display a plurality of activity levels based at least in part on the received second input. In some examples, the baseline activity component 635 may be configured as or otherwise support a means for receiving the input adjusting the baseline activity level for the user is based at least in part on selecting at least one activity level from the plurality of activity levels.

In some examples, selecting the at least one activity level from the plurality of activity levels is based at least in part on a selectable graphical element displayed via the GUI.

In some examples, the selectable graphical element comprises a slider control configured to slide along a slider track of the GUI. In some examples, the baseline activity component 635 may be configured as or otherwise support a means for detecting the input adjusting the baseline activity level based on the slider track of the GUI. In some examples, each activity level of the plurality of activity levels corresponds to a respective node on the slider track.

In some examples, each activity level of the plurality of activity levels are selectable at respective nodes along a minimum to maximum range of the selectable graphical element.

In some examples, each activity level of the plurality of activity levels is based at least in part on a factor of the baseline activity level for the user.

In some examples, the activity type component 655 may be configured as or otherwise support a means for causing the GUI of the device running the application to display a set of activity types for the user, the set of activity types comprising a calorie count for the user or a step count for the user. In some examples, the target activity component 640 may be configured as or otherwise support a means for computing the target activity level for the user is further based at least in part on selecting at least one activity type for the user from the set of activity types for the user.

In some examples, the calorie component 660 may be configured as or otherwise support a means for computing a calorie count level for the user based at least in part on the received physiological data. In some examples, the calorie component 660 may be configured as or otherwise support a means for enabling the application to display the computed calorie count level for the user within the application running on the device and associated with the wearable device based at least in part on a setting for displaying the calorie count level for the user. In some examples, the target activity component 640 may be configured as or otherwise support a means for causing the GUI of the device running the application to display the computed target activity level for the user and the computed calorie count level for the user based at least in part on the enabling.

In some examples, the calorie component 660 may be configured as or otherwise support a means for computing a calorie count level for the user based at least in part on the received physiological data. In some examples, the calorie component 660 may be configured as or otherwise support a means for disabling the application from displaying the computed calorie count level for the user within the application running on the device and associated with the wearable device based at least in part on a setting for displaying the calorie count level for the user. In some examples, the target activity component 640 may be configured as or otherwise support a means for causing the GUI of the device running the application to display the computed target activity level for the user irrespective of the computed calorie count level for the user based at least in part on the disabling.

In some examples, to support causing the GUI of the device running the application to display the computed target activity level for the user irrespective of the computed calorie count level for the user, the calorie component 660 may be configured as or otherwise support a means for refraining from displaying the computed calorie count level for the user within the application running on the device and associated with the wearable device.

In some examples, adjusting the baseline activity level for the user comprises increasing or decreasing the baseline activity level for the user from a default baseline activity level for the user.

In some examples, the score component 630 may be configured as or otherwise support a means for computing a Sleep Score for the user based at least in part on the received physiological data. In some examples, the target activity component 640 may be configured as or otherwise support a means for computing the target activity level for the user is further based at least in part on the adjusted baseline activity level, the computed recovery metric for the user, and the computed Sleep Score for the user.

In some examples, the received physiological data comprises heart rate data associated with the user, heart rate variability data associated with the user, temperature data associated with the user, respiratory rate data associated with the user, blood oxygen data associated with the user, sleep data associated with the user, activity data associated with the user, or any combination thereof.

In some examples, the wearable device comprises a wearable ring device.

Figure 7:
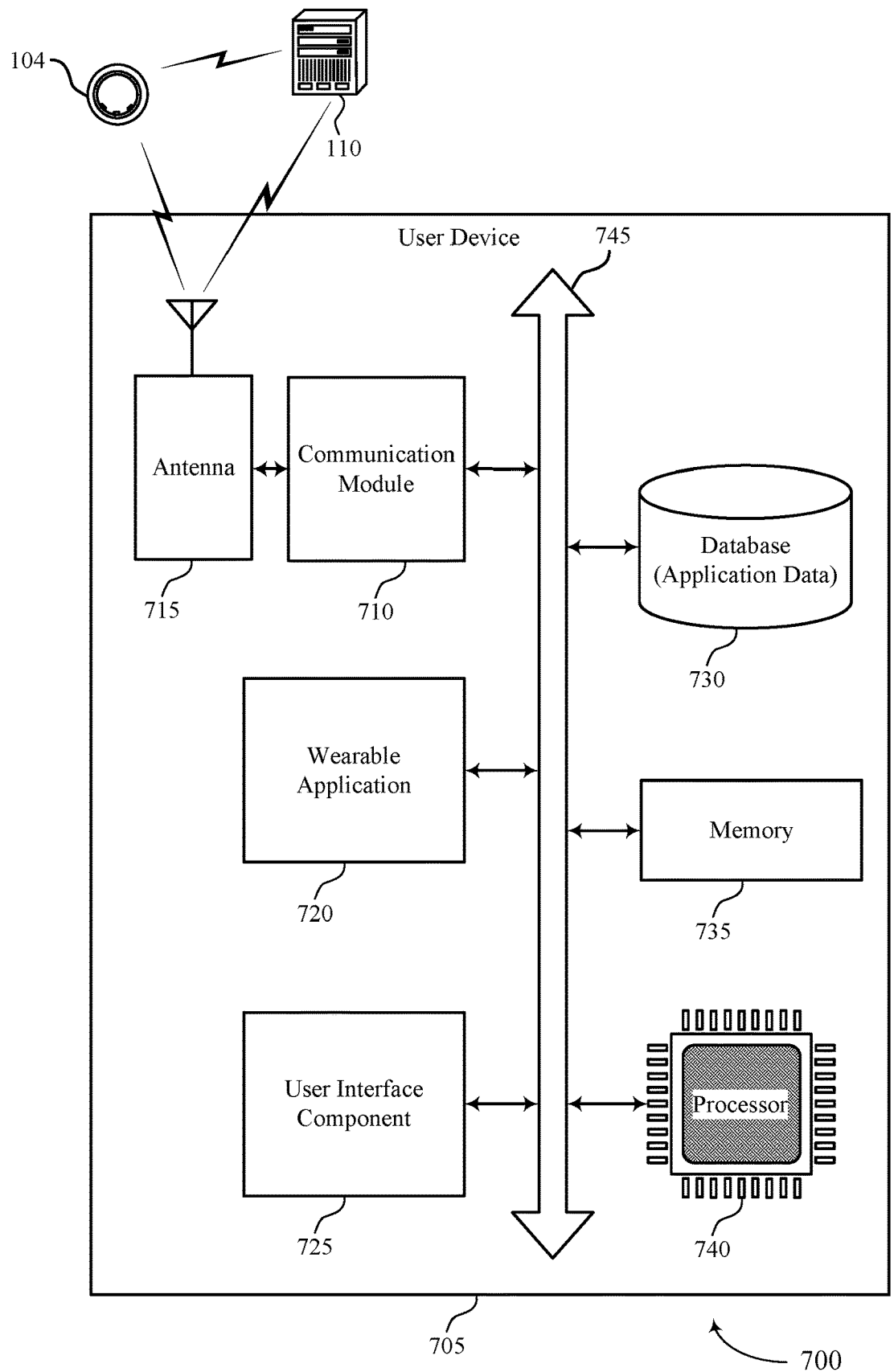
FIG. 7 shows a diagram of a system including a device that supports techniques for activity goal personalization in accordance with aspects of the present disclosure.

FIG. 7 shows a diagram of a system 700 including a device 705 that supports techniques for activity goal personalization in accordance with aspects of the present disclosure. The device 705 may be an example of or include the components of a device 505 as described herein. The device 705 may include an example of a user device 106, as described previously herein. The device 705 may include components for bi-directional communications including components for transmitting and receiving communications with a wearable device 104 and a server 110, such as a wearable application 720, a communication module 710, an antenna 715, a user interface component 725, a database (application data) 730, a memory 735, and a processor 740. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-b of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOS®, ANDROID®, MS-DOS®, MS-WINDOWS®, OS/2®, UNIX®, LINUX®, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715 that may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 735 may contain, among other things, a BIOS that may control basic hardware or software operation such as the interaction with peripheral components or devices.

The processor 740 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

The wearable application 720 may support activity goal personalization at a device in accordance with examples as disclosed herein. For example, the wearable application 720 may be configured as or otherwise support a means for receiving physiological data associated with a user from a wearable device. The wearable application 720 may be configured as or otherwise support a means for computing a recovery metric for the user based at least in part on the received physiological data. The wearable application 720 may be configured as or otherwise support a means for receiving an input adjusting a baseline activity level for the user within an application running on the device and associated with the wearable device. The wearable application 720 may be configured as or otherwise support a means for computing a target activity level for the user based at least in part on the adjusted baseline activity level and the computed recovery metric for the user. The wearable application 720 may be configured as or otherwise support a means for causing a GUI of the device running the application to display the computed target activity level for the user.

By including or configuring the wearable application 720 in accordance with examples as described herein, the device 705 may support techniques for reduced power consumption.

The wearable application 720 may include an application (e.g., "app"), program, software, or other component that may be configured to facilitate communications with a ring 104, server 110, other user devices 106, and the like. For example, the wearable application 720 may include an application executable on a user device 106 that is configured to receive data (e.g., physiological data) from a ring 104, perform processing operations on the received data, transmit and receive data with the servers 110, and cause presentation of data to a user 102.

Figure 8:
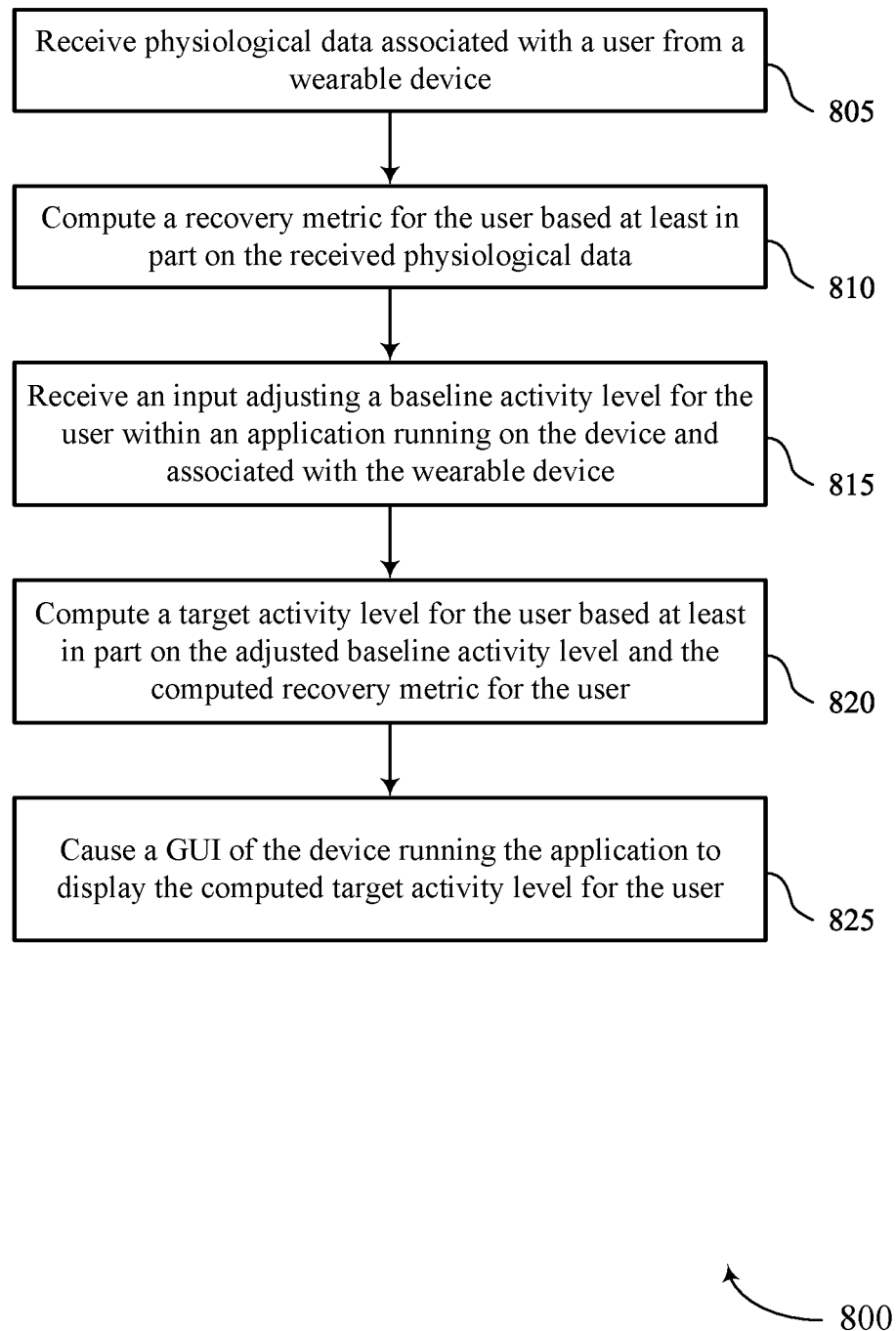
FIG. 8 shows a flowchart illustrating methods that support techniques for activity goal personalization in accordance with aspects of the present disclosure.

FIG. 8 shows a flowchart illustrating a method 800 that supports techniques for activity goal personalization in accordance with aspects of the present disclosure. The operations of the method 800 may be implemented by a user device or its components as described herein. For example, the operations of the method 800 may be performed by a user device as described with reference to FIGS. 1 through 7. In some examples, a user device may execute a set of instructions to control the functional elements of the user device to perform the described functions. Additionally, or alternatively, the user device may perform aspects of the described functions using special-purpose hardware.

At 805, the method may include receiving physiological data associated with a user from a wearable device. The operations of 805 may be performed in accordance with examples as disclosed herein. In some examples, aspects of the operations of 805 may be performed by a physiological data component 625 as described with reference to FIG. 6.

At 810, the method may include computing a recovery metric for the user based at least in part on the received physiological data. The operations of 810 may be performed in accordance with examples as disclosed herein. In some examples, aspects of the operations of 810 may be performed by a score component 630 as described with reference to FIG. 6.

At 815, the method may include receiving an input adjusting a baseline activity level for the user within an application running on the device and associated with the wearable device. The operations of 815 may be performed in accordance with examples as disclosed herein. In some examples, aspects of the operations of 815 may be performed by a baseline activity component 635 as described with reference to FIG. 6.

At 820, the method may include computing a target activity level for the user based at least in part on the adjusted baseline activity level and the computed recovery metric for the user. The operations of 820 may be performed in accordance with examples as disclosed herein. In some examples, aspects of the operations of 820 may be performed by a target activity component 640 as described with reference to FIG. 6.

At 825, the method may include causing a GUI of the device running the application to display the computed target activity level for the user. The operations of 825 may be performed in accordance with examples as disclosed herein. In some examples, aspects of the operations of 825 may be performed by an interface component 645 as described with reference to FIG. 6.

It should be noted that the methods described above describe possible implementations, and that the operations and the steps may be rearranged or otherwise modified and that other implementations are possible. Furthermore, aspects from two or more of the methods may be combined.

A method for activity goal personalization at a device is described. The method may include receiving physiological data associated with a user from a wearable device, computing a recovery metric for the user based at least in part on the received physiological data, receiving an input adjusting a baseline activity level for the user within an application running on the device and associated with the wearable device, computing a target activity level for the user based at least in part on the adjusted baseline activity level and the computed recovery metric for the user, and causing a GUI of the device running the application to display the computed target activity level for the user.

An apparatus for activity goal personalization at a device is described. The apparatus may include a processor, memory coupled with the processor, and instructions stored in the memory. The instructions may be executable by the processor to cause the apparatus to receive physiological data associated with a user from a wearable device, compute a recovery metric for the user based at least in part on the received physiological data, receive an input adjusting a baseline activity level for the user within an application running on the device and associated with the wearable device, compute a target activity level for the user based at least in part on the adjusted baseline activity level and the computed recovery metric for the user, and cause a GUI of the device running the application to display the computed target activity level for the user.

Another apparatus for activity goal personalization at a device is described. The apparatus may include means for receiving physiological data associated with a user from a wearable device, means for computing a recovery metric for the user based at least in part on the received physiological data, means for receiving an input adjusting a baseline activity level for the user within an application running on the device and associated with the wearable device, means for computing a target activity level for the user based at least in part on the adjusted baseline activity level and the computed recovery metric for the user, and means for causing a GUI of the device running the application to display the computed target activity level for the user.

A non-transitory computer-readable medium storing code for activity goal personalization at a device is described. The code may include instructions executable by a processor to receive physiological data associated with a user from a wearable device, compute a recovery metric for the user based at least in part on the received physiological data, receive an input adjusting a baseline activity level for the user within an application running on the device and associated with the wearable device, compute a target activity level for the user based at least in part on the adjusted baseline activity level and the computed recovery metric for the user, and cause a GUI of the device running the application to display the computed target activity level for the user.

Some examples of the method, apparatuses, and non-transitory computer-readable medium described herein may further include operations, features, means, or instructions for receiving a second input to adjust the baseline activity level for the user within the application running on the device and associated with the wearable device, causing the GUI to display a plurality of activity levels based at least in part on the received second input, and wherein receiving the input adjusting the baseline activity level for the user may be based at least in part on selecting at least one activity level from the plurality of activity levels.

Some examples of the method, apparatuses, and non-transitory computer-readable medium described herein may further include operations, features, means, or instructions for selecting the at least one activity level from the plurality of activity levels may be based at least in part on a selectable graphical element displayed via the GUI.

In some examples of the method, apparatuses, and non-transitory computer-readable medium described herein, the selectable graphical element comprises a slider control configured to slide along a slider track of the GUI. Some examples of the method, apparatuses, and non-transitory computer-readable medium described herein may further include operations, features, means, or instructions for detecting the input adjusting the baseline activity level based on the slider track of the GUI. In some examples of the method, apparatuses, and non-transitory computer-readable medium described herein, each activity level of the plurality of activity levels corresponds to a respective node on the slider track.

In some examples of the method, apparatuses, and non-transitory computer-readable medium described herein, each activity level of the plurality of activity levels may be based at least in part on a factor of the baseline activity level for the user.

Some examples of the method, apparatuses, and non-transitory computer-readable medium described herein may further include operations, features, means, or instructions for causing the GUI of the device running the application to display a set of activity types for the user, the set of activity types comprising a calorie count for the user or a step count for the user and wherein computing the target activity level for the user may be further based at least in part on selecting at least one activity type for the user from the set of activity types for the user.

Some examples of the method, apparatuses, and non-transitory computer-readable medium described herein may further include operations, features, means, or instructions for computing a calorie count level for the user based at least in part on the received physiological data, enabling the application to display the computed calorie count level for the user within the application running on the device and associated with the wearable device based at least in part on a setting for displaying the calorie count level for the user, and causing the GUI of the device running the application to display the computed target activity level for the user and the computed calorie count level for the user based at least in part on the enabling.

Some examples of the method, apparatuses, and non-transitory computer-readable medium described herein may further include operations, features, means, or instructions for computing a calorie count level for the user based at least in part on the received physiological data, disabling the application from displaying the computed calorie count level for the user within the application running on the device and associated with the wearable device based at least in part on a setting for displaying the calorie count level for the user, and causing the GUI of the device running the application to display the computed target activity level for the user irrespective of the computed calorie count level for the user based at least in part on the disabling.

In some examples of the method, apparatuses, and non-transitory computer-readable medium described herein, causing the GUI of the device running the application to display the computed target activity level for the user irrespective of the computed calorie count level for the user may include operations, features, means, or instructions for refraining from displaying the computed calorie count level for the user within the application running on the device and associated with the wearable device.

Some examples of the method, apparatuses, and non-transitory computer-readable medium described herein may further include operations, features, means, or instructions for adjusting the baseline activity level for the user comprises increasing or decreasing the baseline activity level for the user from a default baseline activity level for the user.

Some examples of the method, apparatuses, and non-transitory computer-readable medium described herein may further include operations, features, means, or instructions for computing a Sleep Score for the user based at least in part on the received physiological data and wherein computing the target activity level for the user may be further based at least in part on the adjusted baseline activity level, the computed recovery metric for the user, and the computed Sleep Score for the user.

In some examples of the method, apparatuses, and non-transitory computer-readable medium described herein, the received physiological data comprises heart rate data associated with the user, heart rate variability data associated with the user, temperature data associated with the user, respiratory rate data associated with the user, blood oxygen data associated with the user, sleep data associated with the user, activity data associated with the user, or any combination thereof.

In some examples of the method, apparatuses, and non-transitory computer-readable medium described herein, the wearable device comprises a wearable ring device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for activity goal personalization at a device, comprising:
    identifying a baseline activity level for a user;
    receiving, via a first graphical element within an application running on a graphical user interface of the device, a first input indicating a request to adjust the baseline activity level for the user;
    causing the graphical user interface of the device to display a second graphical element within the application in response to the request to adjust the baseline activity level, the second graphical element comprising a slider control and a plurality of nodes along a slider track, each node along the slider track corresponding to a respective adjusted value of the baseline activity level;
    receiving, via the second graphical element, a second input that manipulates the slider control along the slider track to select a first node of the plurality of nodes, the first node corresponding to a first adjusted value of the baseline activity level;
    receiving physiological data associated with the user from a wearable device;
    computing a recovery metric for the user based at least in part on the physiological data;
    computing a target activity level for the user based at least in part on the first adjusted value of the baseline activity level and the recovery metric for the user; and
    causing the graphical user interface of the device running the application to display the target activity level for the user.

2. The method of claim 1, further comprising:
    causing the graphical user interface to display a plurality of activity levels based at least in part on the first input,
    wherein receiving the second input adjusting the baseline activity level for the user is based at least in part on selecting at least one activity level from the plurality of activity levels.

3. The method of claim 2, wherein selecting the at least one activity level from the plurality of activity levels is based at least in part on the second graphical element displayed via the graphical user interface.

4. The method of claim 3, wherein each activity level of the plurality of activity levels are selectable at respective nodes along a minimum to maximum range of the slider track.

5. The method of claim 2, wherein each activity level of the plurality of activity levels is based at least in part on a factor of the baseline activity level for the user.

6. The method of claim 1, further comprising:
    causing the graphical user interface of the device running the application to display a set of activity types for the user, the set of activity types comprising a calorie count for the user or a step count for the user,
    wherein computing the target activity level for the user is further based at least in part on selecting at least one activity type for the user from the set of activity types for the user.

7. The method of claim 1, further comprising:
    computing a calorie count level for the user based at least in part on the physiological data;
    enabling the application to display the calorie count level for the user within the application running on the device and associated with the wearable device based at least in part on a setting for displaying the calorie count level for the user; and
    causing the graphical user interface of the device running the application to display the target activity level for the user and the calorie count level for the user based at least in part on the enabling.

8. The method of claim 1, further comprising:
    computing a calorie count level for the user based at least in part on the physiological data;
    disabling the application from displaying the calorie count level for the user within the application running on the device and associated with the wearable device based at least in part on a setting for displaying the calorie count level for the user; and
    causing the graphical user interface of the device running the application to display the target activity level for the user irrespective of the calorie count level for the user based at least in part on the disabling.

9. The method of claim 8, wherein causing the graphical user interface of the device running the application to display the target activity level for the user irrespective of the calorie count level for the user comprises:
refraining from displaying the calorie count level for the user within the application running on the device and associated with the wearable device.

10. The method of claim 1, wherein adjusting the baseline activity level for the user comprises increasing or decreasing the baseline activity level for the user from a default baseline activity level for the user.

11. The method of claim 1, further comprising:
computing a Sleep Score for the user based at least in part on the physiological data,
wherein computing the target activity level for the user is further based at least in part on the respective adjusted value of the baseline activity level, the recovery metric for the user, and the Sleep Score for the user.

12. The method of claim 1, wherein the physiological data comprises heart rate data associated with the user, heart rate variability data associated with the user, temperature data associated with the user, respiratory rate data associated with the user, blood oxygen data associated with the user, sleep data associated with the user, activity data associated with the user, or any combination thereof.

13. The method of claim 1, wherein the wearable device comprises a wearable ring device.

14. An apparatus for activity goal personalization, comprising:
one or more processors;
one or more memories coupled with the one or more processors; and
instructions stored in the one or more memories and executable by the one or more processors to cause the apparatus to:
identify a baseline activity level for a user;
receive, via a first graphical element within an application running on a graphical user interface of the apparatus, a first input indicating a request to adjust the baseline activity level for the user;
cause the graphical user interface of the apparatus to display a second graphical element within the application in response to the request to adjust the baseline activity level, the second graphical element comprising a slider control and a plurality of nodes along a slider track, each node along the slider track corresponding to a respective adjusted value of the baseline activity level;
receive, via the second graphical element, a second input that manipulates the slider control along the slider track to select a first node of the plurality of nodes, the first node corresponding to a first adjusted value of the baseline activity level;
receive physiological data associated with the user from a wearable device;
compute a recovery metric for the user based at least in part on the physiological data;
compute a target activity level for the user based at least in part on the first adjusted value of the baseline activity level and the recovery metric for the user; and
cause the graphical user interface of the apparatus running the application to display the target activity level for the user.

15. The apparatus of claim 14, wherein the instructions are further executable by the one or more processors to cause the apparatus to:
cause the graphical user interface to display a plurality of activity levels based at least in part on the first input, wherein the instructions to receive the second input adjusting the baseline activity level for the user are further executable by the one or more processors based at least in part on selecting at least one activity level from the plurality of activity levels.

16. The apparatus of claim 15, wherein the instructions to select the at least one activity level from the plurality of activity levels are further executable by the one or more processors based at least in part on the second graphical element displayed via the graphical user interface.

17. The apparatus of claim 16, wherein each activity level of the plurality of activity levels are selectable at respective nodes along a minimum to maximum range of the slider track.

18. The apparatus of claim 15, wherein each activity level of the plurality of activity levels is based at least in part on a factor of the baseline activity level for the user.

19. The apparatus of claim 14, wherein the instructions are further executable by the one or more processors to cause the apparatus to:
cause the graphical user interface of the apparatus running the application to display a set of activity types for the user, the set of activity types comprising a calorie count for the user or a step count for the user,
wherein the instructions compute the target activity level for the user are further executable by the one or more processors based at least in part on selecting at least one activity type for the user from the set of activity types for the user.

20. A non-transitory computer-readable medium storing code for activity goal personalization at a device, the code comprising instructions executable by a processor to:
identify a baseline activity level for a user;
receive, via a first graphical element within an application running on a graphical user interface of the device, an input indicating a request to adjust the baseline activity level for the user;
cause the graphical user interface of the device to display a second graphical element within the application in response to the request to adjust the baseline activity level, the second graphical element comprising a slider control and a plurality of nodes along a slider track, each node along the slider track corresponding to a respective adjusted value of the baseline activity level;
receive, via the second graphical element, a second input that manipulates the slider control along the slider track to select a first node of the plurality of nodes, the first node corresponding to a first adjusted value of the baseline activity level;
receive physiological data associated with the user from a wearable device;
compute a recovery metric for the user based at least in part on the physiological data;
compute a target activity level for the user based at least in part on the first adjusted value of the baseline activity level and the recovery metric for the user; and
cause the graphical user interface of the device running the application to display the target activity level for the user.

* * * * *